United States Patent
Luo et al.

(10) Patent No.: US 9,849,118 B2
(45) Date of Patent: Dec. 26, 2017

(54) PROTEIN TYROSINE PHOSPHATASE INHIBITOR, PREPARATION METHOD AND USES THEREOF

(71) Applicant: HEBEI UNIVERSITY, Baoding, Hebei (CN)

(72) Inventors: Duqiang Luo, Baoding (CN); Jun Zhang, Baoding (CN); Zhiqin Liu, Baoding (CN)

(73) Assignee: Heibei University (CN)

( * ) Notice: Subject to any disclaimer, the term of this patent is extended or adjusted under 35 U.S.C. 154(b) by 0 days.

(21) Appl. No.: 14/403,113

(22) PCT Filed: May 7, 2013

(86) PCT No.: PCT/CN2013/075235
§ 371 (c)(1),
(2) Date: Nov. 21, 2014

(87) PCT Pub. No.: WO2013/174207
PCT Pub. Date: Nov. 28, 2013

(65) Prior Publication Data
US 2015/0148545 A1    May 28, 2015

(30) Foreign Application Priority Data

May 22, 2012   (CN) .......................... 2012 1 0158554

(51) Int. Cl.
| | | |
|---|---|---|
| *A61K 31/4412* | (2006.01) | |
| *C07D 213/89* | (2006.01) | |
| *C12P 17/12* | (2006.01) | |
| *A61K 9/00* | (2006.01) | |
| *A61K 9/14* | (2006.01) | |
| *A61K 9/20* | (2006.01) | |
| *A61K 9/48* | (2006.01) | |

(52) U.S. Cl.
CPC ........ *A61K 31/4412* (2013.01); *A61K 9/0019* (2013.01); *A61K 9/0053* (2013.01); *A61K 9/14* (2013.01); *A61K 9/20* (2013.01); *A61K 9/48* (2013.01); *C07D 213/89* (2013.01); *C12P 17/12* (2013.01)

(58) Field of Classification Search
CPC .............. A61K 31/4412; A61K 9/0019; A61K 9/0053; A61K 9/14; A61K 9/48; A61K 213/89; A61K 17/12
See application file for complete search history.

(56) References Cited

FOREIGN PATENT DOCUMENTS

| | | |
|---|---|---|
| CN | 102234231 A | 11/2011 |
| CN | 102675199 A | 9/2012 |
| EP | 0445920 A2 | 9/1991 |

OTHER PUBLICATIONS

Isaka et al. "Bioactive Substances from Insect Pathogenic Fungi" 2005 Acc Chem Res. vol. 38: 813-823.*

* cited by examiner

*Primary Examiner* — Robert Yamasaki
*Assistant Examiner* — Teresa E Knight
(74) *Attorney, Agent, or Firm* — Harness, Dickey & Pierce, P.L.C.

(57) ABSTRACT

Disclosed in the present invention is a protein tyrosine phosphatase inhibitor. The preparation method therefor is: extracting the crude product from the *Isaria Fumosorosea Wize* solid or liquid fermentation broth using ethyl acetate, ethanol, methanol, or a mixed solvent of chloroform and methanol; separating the obtained extract using column chromatography on silica gel; and obtaining the target product. The inhibitor can be used to prepare pharmaceutical compositions for treating and preventing diabetes, obesity and cancers.

4 Claims, No Drawings

PROTEIN TYROSINE PHOSPHATASE INHIBITOR, PREPARATION METHOD AND USES THEREOF

CROSS-REFERENCE TO RELATED APPLICATIONS

This application is a U.S. National Stage Application of International Application No. PCT/CN2013/075235 filed on May 7, 2013, and published in Chinese as WO 2013/174207 A1 on Nov. 28, 2013. This application claims priority to Chinese Application No. 201210158554.5 filed on May 22, 2012. The entire disclosures of the above applications are incorporated herein by reference.

FIELD OF THE INVENTION

The present invention relates to a protein tyrosine phosphatase inhibitor, to method for preparing the same, and to use thereof in the manufacture of a pharmaceutical composition for the treatment and prevention of diabetes, obesity and cancers.

BACKGROUND OF THE INVENTION

Protein tyrosine phosphatases (PTPs) belong to signal-transduction enzymes. They regulate cell growth, differentiation and metabolism by modulating the phosphorylation level of intracellular tyrosine. PTPs also regulate cell migration, genetic transcription, opening and closing of an ion channel, immune response, apoptosis and osteoblastic development. PTPs disorder may result in a variety of diseases such as cancer, diabetes, obesity and osteoporosis. To date, there has been found more than 130 gene-encoding PTPs in human genome. These highly specific PTPs are not only associated with the signal pathway of the inhibition and occurrence of cancers, but can also directly lead to the onset of different diseases in human due to their dysfunctions. The action mechanisms of PTPs associated with the onset of diseases as well as the screening of their inhibitors are always the hot focus of the word.

PTPases which include a large family of transmembrane (receptor type) and intracellular (non-receptor type) enzymes are involved in regulation of a series of vital life processes. Several PTPases may affect the action of insulin at the receptor or post-receptor stage in the insulin pathway. Currently, studies mainly focus on the research of SHP-2 and PTP1B.

PTP1B is the first protein tyrosine phosphatase that has been successfully isolated. This enzyme is an intracellular enzyme of 37 kD. It anchors onto the endoplasmic reticulum via the 35 amino acid residues-containing C-terminal. Cysteine at the 215$^{th}$ position is the catalytic active site of PTB1. Studies have shown that PTP1B blocks the signal transduction pathway of insulin via Insulin Receptor (IR) and Insulin Receptor Substrate (IRS) and ultimately affects the transportation of glucose from blood into cells, which represents as an elevated blood glucose. In addition, since PTP1B gene knockout mice are immune to obesity, it can be determined definitely that PTP1B plays a key role in the pathogenesis of obesity. Consequently, PTP1B is a target of the development of new medicaments for the treatment of diabetes and obesity.

Protein tyrosine phosphatase SHP2 [Src homology 2 (SH2) domain containing phosphotyrosinephosphatase 2] is a non-receptor type protein tyrosine phosphatase (PTP) which is encoded by PTPN11 gene and widely expressed in cytoplasm. SHP2 plays a key role in processes such as cell proliferation and differentiation by participating in a variety of intracellular signal transductions, such as MAP kinase pathway. Jak-Stat pathway, PI3 kinase pathway and other pathways. PTPN11 is identified as a proto-oncogene and also involves in the signal pathways of many other proto-oncogenes as an important member. Hence, SHP2 serves as a potential drug target for the treatment of diseases such as Noonan syndrome and juvenile myelomonocytic leukemia, as well as other possible relevant tumor diseases.

Up to date, there is no report yet available in the prior art concerning the extraction of a protein tyrosine phosphatase inhibitor from the fermentation product of *Isaria Fumosorosea Wize*.

SUMMARY OF THE INVENTION

The technical problem to be solved by the present invention is to provide a novel protein tyrosine phosphatase inhibitor, method for preparing the same and use thereof in the manufacture of a pharmaceutical composition for the treatment and prevention of diabetes, obesity and cancers.

To solve the technical problem mentioned above, the technical solution employed in the invention is as follows:

A protein tyrosine phosphatase inhibitor, which is the following (a) or (b):

(a) a compound having the following structural formula:

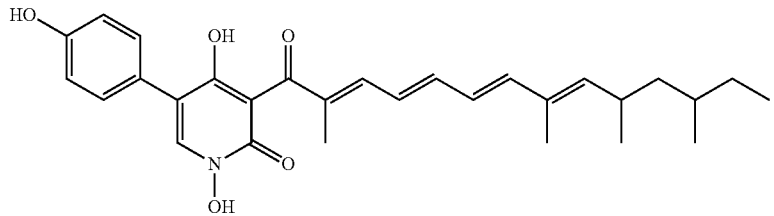 [SMILES: CCC(C)CC(C)/C=C(C)/C=C/C=C/C=C(\C)C(=O)c1c(O)c(-c2ccc(O)cc2)cn(O)c1=O]

(b) an isomer of the above compound or a pharmaceutically acceptable derivative thereof.

As a preferred technical solution of the invention, the pharmaceutically acceptable derivative thereof is a pharmaceutically acceptable salt, which maintains the biological effectiveness of said (a) and is an acid addition salt or base addition salt commonly used in pharmacy and derived from non-toxic organic acids (e.g., carboxylic acid having from 1 to 20 carbon atoms, sulfonic acid, amino acid, sulfamic acid, or substituents thereof), inorganic acids, organic bases or inorganic bases.

As a preferred technical solution of the invention, the inorganic acids used for preparing said acid addition salt are hydrochloric acid, hydrobromic acid, hydroiodic acid, sulfuric acid, sulfamic acid, phosphoric acid or nitric acid. The organic acids used for preparing said acid addition salt are p-toluenesulfonic acid, salicylic acid, methanesulfonic acid, oxalic acid, malic acid, succinic acid, lactic acid, fumaric acid. The basic agents used for preparing said base addition salt are hydroxides of alkali metal, alkali earth metal and quaternary ammonium; bicarbonates of alkali metal, alkali earth metal and quaternary ammonium; carbonates of alkali metal, alkali earth metal and ammonium; organic ammonium having from 1 to 30 carbon atoms; substituted pyridine and quinoline; particularly hydroxides of ammonium, potassium, sodium or quaternary ammonium, such as tetramethylammonium hydroxide.

As a preferred technical solution of the invention, the pharmaceutically acceptable derivative thereof is in the form of ester or ether derivative; or it is incorporated with a functional group of aldehyde, acid or alcohol by oxidation of double bonds; or it is incorporated with sulfonic acid group in the ring; or it is incorporated with a chain having from 4 to 10 carbon atoms by Witting reaction; or part of or all of the double bonds on the side chain thereof are saturated; or it is incorporated on the side chain with one group or a combination of more groups selected from the group consisting of alcohol, aldehyde, ether, thioether, sulfoxide, sulphone, halogen, carboxylic acid, sulfonic acid, amine, amide, sulfamide, saturated or unsaturated alkyl, cycloalkyl, fused alkyl and fused aryl group; or it is incorporated in one or two rings with one group or a combination of more groups selected from the group consisting of alcohol, aldehyde, ether, thioether, sulfoxide, sulphone, halogen, carboxylic acid, ester, sulfonic acid, amine, amide, sulfamide, saturated or unsaturated alkyl, cycloalkyl, fused alkyl and fused aryl.

As a preferred technical solution of the invention, the chain incorporated by Witting reaction carries $OR^1$, $NR^2R^3$ or halogen, wherein $R^1$, $R^2$ or $R^3$ is H or alkyl having from 1 to 5 carbon atoms, and halogen is F, Cl, Br or I.

A method for preparing the above-mentioned protein tyrosine phosphatase inhibitor comprises: extracting a solid or liquid fermentation broth of entomogenous fungus *Isaria Fumosorosea Wize* with ethyl acetate, ethanol, methanol, or a mixed solvent of chloroform and methanol; and separating the resulting extract by column chromatography on silica gel to obtain Fumosorinone, namely, the protein tyrosine phosphatase inhibitor (a) according to the first aspect of the disclosure.

As a preferred technical solution for the above-mentioned preparation method, it comprises:

A. Fermentation and Cultivation: inoculating the *Isaria Fumosorosea Wize* strain to a modified potato dextrose culture medium with an inoculation needle; culturing the mixture in a shaker at 150 rpm and at 26° C. for 7 days to obtain a seed broth; inoculating the seed broth to a rice culture medium and culturing under light at 26° C. for 30 days to obtain a fermented product; wherein, the said modified potato dextrose culture medium is formulated by the following steps: dissolving 200 parts by weight of peeled potato, 20 parts by weight of dextrose, 3 parts by weight of $KH_2PO_4$, 1.5 parts by weight of $MgSO_4$, 0.1 parts by weight of citric acid, and 0.01 parts by weight of vitamin $B_1$ in 1000 parts by weight of sterile water, and adjusting pH to 6.5 and sterilizing at 121° C. for 20 minutes; and the rice culture medium is formulated by the following steps: dissolving 80 parts by weight of rice in 100 parts by weight of sterile water, soaking for 12 hours, and then at natural sterilizing at 1.21° C. for 30 minutes;

B. Extraction and Separation: extracting the fermented product by soaking it in equal volume of ethyl acetate at room temperature for 48 hours; evaporating to dryness by vacuum distillation with a rotatory evaporator at 45° C. to obtain an extractum sample; thoroughly mixing said extractum sample with 1.2 times by weight of silica gel having mesh size of 100 to 200 under stirring, drying and grinding uniformly to obtain powders, rendering said extractum sample sufficiently absorbed onto the silica gel particles; then performing atmospheric column chromatography on silica gel having a mesh size ranging from 300 to 400, and eluting gradiently with petroleum ether/ethyl acetate system in ratios of 100:0, 95:5, 0:10, 80:20, 60:40 and 50:50 (v/v); collecting the eluents, evaporating by vacuum distillation at 45° C., concentrating and washing with an organic solvent; further subjecting the fraction obtained from the above elution section with 80:20 of petroleum ether/ethyl acetate to the above-mentioned atmospheric column chromatography on silica gel, and eluting gradiently again with petroleum ether/ethyl acetate system in ratios of 100:0, 50:1, 20:1, 15:1, 10:1 and 5:1 (v/v); collecting the eluents, evaporating by vacuum distillation at 45° C. to obtain Fumosorinone at the 5:1 elution section, namely, to obtain the protein tyrosine phosphatase inhibitor (a) according to the first aspect of the disclosure.

As a preferred technical solution for the above-mentioned preparation method, it comprises:

A. Fermentation and Cultivation: inoculating the *Isaria Fumosorosea Wize* strain to a modified potato dextrose culture medium with an inoculation needle; culturing the mixture in a shaker at 150 rpm and at 26° C. for 7 days to obtain a seed broth; inoculating the seed broth to a rice culture medium and culturing under light at 26° C. for 30 days to obtain a fermented product; wherein, the said modified potato dextrose culture medium is formulated by the following steps: dissolving 200 parts by weight of peeled potato, 20 parts by weight of dextrose, 3 parts by weight of $KH_2PO_4$, 1.5 parts by weight of $MgSO_4$, 0.1 parts by weight of citric acid, and 0.01 parts by weight of vitamin $B_1$ in 1000 parts by weight of sterile water, and adjusting pH to 6.5 and sterilizing at 121° C. for 20 minutes; and the said rice culture medium is formulated by the following steps: dissolving 80 parts by weight of rice in 100 parts by weight of sterile water, soaking for 12 hours, and then at natural pH sterilizing at 121° C. for 30 minutes;

B. Extraction and Separation: extracting the fermented product by soaking it in equal volume of ethyl acetate at room temperature for 48 hours; evaporating to dryness by vacuum distillation with a rotatory evaporator at 45° C. to obtain an extractum sample; thoroughly mixing said extractum sample with 1.2 times by weight of silica gel having a mesh size of 100 to 200 under stirring, drying and grinding uniformly to obtain powders, rendering said extractum sample sufficiently absorbed onto the silica gel particles; then conducting atmospheric column chromatography on silica gel having a mesh size ranging from 300 to 400, and eluting gradiently with petroleum ether/ethyl acetate system in ratios of 100:0, 95:5, 90:10, 80:20, 60:40 and 50:50 (v/v); collecting the eluents, evaporating by vacuum distillation at 45° C., concentrating and washing with an organic solvent; combining the eluents from each elution section, performing the above-mentioned atmospheric column chromatography on silica gel again, and eluting gradiently with petroleum ether/ethyl acetate system in ratios of 100:0, 50:1, 20:1, 15:1, 10:1 and 5:1 (v/v) again; collecting the eluents, evaporating by vacuum distillation at 45° C.; combining the fractions from each elution section again, and repeating the gradient elution with petroleum ether/ethyl acetate in ratios of 100:0, 50:1, 20:1, 15:1, 10:1 and 5:1 (v/v) to obtain Fumosorinone at the 5:1 elution section, namely, to obtain the protein tyrosine phosphatase inhibitor (a) according to the first aspect of the disclosure.

As a preferred technical solution for the above-mentioned preparation method, it comprises:

A. Fermentation and Cultivation: inoculating the *Isaria Fumosorosea Wize* strain to a modified potato dextrose culture medium with an inoculation needle; culturing the mixture in a shaker at 150 rpm and at 26° C. for 7 days to obtain a seed broth; inoculating the seed broth to a rice culture medium and culturing under light at 26° C. for 30 days to obtain a fermented product; wherein, the said modified potato dextrose culture medium is formulated by the following steps: dissolving 200 parts by weight of peeled potato, 20 parts by weight of dextrose, 3 parts by weight of $KH_2PO_4$, 1.5 parts by weight of $MgSO_4$, 0.1 parts by weight of citric acid, and 0.01 parts by weight of vitamin $B_1$ in 1000 parts by weight of sterile water, and adjusting pH to 6.5 and sterilizing at 121° C. for 20 minutes; and the said rice culture medium is formulated by the following steps: dissolving 80 parts by weight of rice in 100 parts by weight of sterile water, soaking for 12 hours, and then at natural pH sterilizing at 121° C. for 30 minutes:

B. Extraction and Separation: extracting the fermented product by soaking it in equal volume of ethyl acetate at room temperature for 48 hours; evaporating to dryness by vacuum distillation with a rotatory evaporator at 45° C. to obtain an extractum sample; thoroughly mixing said extractum sample with 1.2 time by weight of silica gel having a mesh size of 100 to 200 under stirring, drying and grinding uniformly to obtain powders, rendering said extractum sample sufficiently absorbed onto the silica gel particles; then performing atmospheric column chromatography on silica gel having a mesh size ranging from 300 to 400, eluting gradiently with petroleum ether/ethyl acetate system in ratios of 100:0, 95:5, 90:10, 80:20, 60:40 and 50:50 (v/v); collecting the eluents, evaporating by vacuum distillation at 45° C., concentrating and washing with an organic solvent; further subjecting the fraction obtained from the above elution section with 80:20 of petroleum ether/ethyl acetate to the above-mentioned atmospheric column chromatography on silica gel, and eluting gradiently with chloroform/methanol in ratios of 100:0, 95:5 and 90:10 (v/v) to obtain Fumosorinone at the 90:10 elution section, namely, to obtain the protein tyrosine phosphatase inhibitor (a) according to the first aspect of the disclosure.

Use of the above-mentioned protein tyrosine phosphatase inhibitor in the manufacture of a pharmaceutical composition for the treatment and prevention of diabetes, obesity and cancers.

The beneficial effects produced by the above-mentioned technical solutions lie in that: the inventors have verified the actual effects of compound (a) of the invention by experiments, in particular as follows:

① In-Vitro Inhibition Experiment of Compound (a) of the Invention on Protein Tyrosine Phosphatase PTP1B.

Enzyme: human PTP1B was cloned from cDNA library by conventional molecular biological methods. The cDNA sequence was identical with that of the public human PTP1B (Accession No. M33689). The protein was expressed and purified from *E. coli*, as described in Barford D. et al., J. Mol Biol (1994) 239, 726-730. A phosphorylated tyrosine peptide based on the amino acid sequence at tyrosine autophosphorylation site 1146 (TRDI(Py)E) of the insulin receptor was used as the substrate. Reaction conditions were as follows: PTP1B (05-2 Nm) was incubated with the compound for 15 minutes in a buffer containing 37.5 nM Bis-Tris (at pH 6.2), 140 nM NaCl, 0.05% BSA and 2 Mm DTT. The reaction was initiated with the addition of 50 μM substrate under room temperature (22-25□) and terminated with KOH. Malachite green was used to detect the amount of phosphate. The experimental result shows that: the inhibitory activity ($IC_{50}$) of Fumosorinone, namely the protein tyrosine phosphatase inhibitor of the invention, on protein tyrosine phosphatase PTP1B is 0.42 μg/ml.

② In-Vitro Inhibition Experiment of Compound (a) of the Invention on Protein Tyrosine Phosphatase SHP2.

Enzyme: human SHP2 was cloned from cDNA library by conventional molecular biological methods. The cDNA sequence was identical with that of the public human SHP2 (Accession No. M002834). The protein was expressed and purified from *E. coli*, as described in Ute Dechert. et al., J. Biol Chem, 1994, 269(8): 5602-5611. SHP2 hydrolyzed the phosphate group of pNPP (p-nitrophenyl phosphate), and the product pNP (p-nitrophenol) showed absorbance at 405 nm. The absorbance value increased in positive proportion to the time of enzymatic reaction. Hence, it was possible to reflect initial rate of enzymatic reaction according to the slope of the increased absorbance curve and determine the activity of SHP2. The enzymatic reaction system components was as follows: a buffer (50 mM Bis-Tris at pH 6.0, 2 mM DTT, 2 mM EDTA, GST2-SHP2, and 2 mM pNPP). The enzymatic activity was calculated by dynamically measuring the absorbance value at the wavelength of 405 nm under room temperature after uniformly mixing of the reaction system. The experimental result shows that: the inhibitory activity ($IC_{50}$) of Fumosorinone, namely the protein tyrosine phosphatase inhibitor of the invention, on protein tyrosine phosphatase SHP2 is 0.90 μg/ml.

③ In-Vivo Verification of the Hypoglycemic Effect of Compound (a) of the Invention.

An animal model of experimental diabetes was established by damaging pancreas or islet cells, thereby leading to insulin-deficiency, or by using an antagonist against the action of insulin, resulting in experimental diabetes or experimental hyperglycemia. Alloxan-induced diabetic model is the most common model in the current research on human diabetes, and alloxan-induced diabetic mouse model was used to test the portion of hypoglycemic activity among the activities of the target compound.

Establishment of the experimental animal model of diabetes: Male mice (of *Kunming* species) were purchased and fed for three days, and they were adapted to the environment before experiment. Mice of similar weights (26±2 g) were fasted for 16 to 18 hours and then intraperitoneally injected with 1% of alloxan saline solution (prepared before use) one time or multiple times in succession in a dose of 200 mg/kg. Multiple injections were performed at an interval of 3 days and were performed consecutively for 4 times with an alloxan solution in the same dose. Blood samples were taken from tails of the mice under non-fasting state at 48 hours after injection, and the blood glucose value was measured. The standard value was set as blood glucose value>12.0 mmol/l. Mice whose blood glucose values failed to return to normal value after one week were identified as mouse model of diabetes and defined as the diabetic group. Mice in the normal control group were intraperitoneally injected with saline in the same dose.

Grouping and treatment of the experimental animals: there were six groups of mouse model of diabetes, namely, 10 mice of the normal control group, 10 mice (with blood glucose value>12 mmol/l) of the model control group, 10 mice of the positive control group and 30 mice of the experimental groups (i.e. groups of target compound in low, medium and high doses). After being classified into each group, mice were administered by gavage. Mice from the normal control group and the model control group were administered with normal saline. Mice from the positive control group were daily administered by gavage with 50 mg/kg of gliclazide. Mice from said three experimental groups were respectively administered by gavage with a saline solution of the target compound in different doses (12.5 mg/kg, 25 mg/kg, and 50 mg/kg), twice a clay (one before noon and the other after noon), each time in half dose.

Measurement of blood glucose: blood samples were taken from the tail vein of mice that had been fasted for 16 to 18 hours, respectively at the $5^{th}$ day, $10^{th}$ day and $15^{th}$ day after administration, and the blood glucose was measured.

Experimental result: see table 1. As compared with those from the model control group, 5 days after administration by gavage, mice from the respective drug-administered groups showed decreased blood glucose values.

TABLE 1

Table 1. Effect of the target compound on the blood glucose of mice with alloxan-induced diabetes.

| Group | dose (mg/kg) | blood glucose concentration (mmol/L) 0 d | blood glucose concentration (mmol/L) 5 d | blood glucose concentration (mmol/L) 10 d | blood glucose concentration (mmol/L) 15 d |
|---|---|---|---|---|---|
| Normal control group | — | 4.23 ± 0.48aA | 4.6 ± 0.45aA | 5.18 ± 1.83aB | 4.28 ± 0.89aA |
| Model control group | — | 23.8 ± 2.36bA | 24.6 ± 1.35bA | 25.1 ± 3.34bA | 25.64 ± 1.56bA |
| Positive control group | 50 | 24.4 ± 3.21bA | 21.2 ± 2.89cB | 19.3 ± 1.12cC | 15.4 ± 2.26cD |
| Low-dose group | 12.5 | 23.8 ± 4.32bA | 22.8 ± 2.68cA | 18.4 ± 1.38cB | 15.3 ± 2.21cC |
| Medium-dose group | 25 | 24.1 ± 3.35bA | 20.6 ± 1.87cB | 17.8 ± 2.38cC | 12.9 ± 2.72dD |
| High-dose group | 50 | 23.6 ± 2.84bA | 12.16 ± 4.36cA | 10.34 ± 2.31dB | 6.32 ± 3.2eC |

Note:
different lowercase letters in the same column indicated that the blood glucose values of mice from different groups were significantly different at the level of $P < 0.05$; different uppercase letters in the same line indicated that the blood glucose values of mice at different times after administration were significantly different at the level of $P < 0.05$.

④ According to the common knowledge of pharmacy, compound (a) of the invention can produce a variety of derivatives having similar effects by simple chemical reactions. The actual effects of these derivatives are expectable to those skilled in the art.

DETAILED DESCRIPTION OF THE INVENTION

The invention is illustrated by the following examples. All starting materials and equipment employed in the invention are conventional and commercially available and can be directly purchased from the market.

Example 1: Preparation of the Product

The *Isaria Fumosorosea Wize* (=*Paecilomyces fumosoroseus* (Wize) A. H. S. Br. & G. Sm) used in the invention was collected from Baoding city, Hebei Province; and the strain was kept at the College of Life Science, Hebei University. For specific source, please refer to the Disclosure Form of the Origin of Genetic Resources. The *Isaria Fumosorosea Wize* has been deposited at the Agricultural Culture Collection of China (ACCC; 12 Zhongguancun South Street, Haidian District, Beijing) on Mar. 31, 2009 under the deposit (accession) number 37775.

A. Fermentation and Cultivation: *Isaria Fumosorosea Wize* strain was inoculated with an inoculation needle into a 500 ml Erlenmeyer flask containing 100 ml of modified potato dextrose culture medium (formulated by dissolving 200.0 g of peeled potato, 20.0 g of dextrose, 3.0 g of $KH_2PO_4$, 1.5 g of $MgSO_4$, 0.1 g of citric acid, and 10.0 mg of vitamin $B_1$ in 1 l of sterile water, pH 6.5 and sterilizing at 121° C. for 20 minutes). The mixture was cultured in a shaker at 150 rpm and at 26° C. for 7 days, to obtain a seed broth. 10 nil of the seed broth was inoculated into a 500 ml Erlenmeyer flask containing rice culture medium (formulated by dissolving 80 g of rice in 100 ml of sterile water, soaking for 12 hours, and then at natural pH sterilizing at 121° C. for 30 minutes). There were 50 Erlenmeyer flasks in total. The mixture was further cultured under light at 26° C. for 30 days.

B. Extraction and Separation: the fermented product was extracted by soaking with equal volume of ethyl acetate at room temperature for 48 hours, and evaporated to dryness by vacuum distillation with a rotatory evaporator at 45° C. for three times, to obtain 200 g of extractum sample. Said extractum sample was thoroughly mixed with 240 g of silica gel (with a mesh size of 100 to 200) under stirring, dried, ground uniformly to obtain powders, rendering said extractum sample sufficiently absorbed onto the silica gel particles. The mixture was then subjected to atmospheric column chromatography on silica gel (with a mesh size ranging from 300 to 400), and eluted gradiently with petroleum ether/ethyl acetate system (100:0, 95:5, 90:10, 80:20, 60:40 and 50:50 (v/v)). The eluents were collected in 500 ml triangular flasks, subjected to vacuum distillation at 45° C., concentrated and washed with a small amount of organic solvent. The resulting samples were placed in 5 ml flaskets and the flaskets were numbered and labeled. 37 g of the fraction obtained from the elution section with 80:20 of petroleum ether/ethyl acetate was further subjected to atmospheric column chromatography on silica gel under gradient elution with petroleum ether/ethyl acetate system (100:0, 50:1, 20:11, 15:1, 10:1 and 5:1 (v/v)). The eluents were collected in 200 ml triangular flasks and subjected to vacuum distillation at 45° C., to obtain 10 g of Fumosorinone at the 5:1 elution section, namely, to obtain the protein tyrosine phosphatase inhibitor (a).

Example 2: Preparation of the Product

This example differed from example 1 in the following procedures: the extractum sample, after being sufficiently adsorbed on the silica gel particles, was subjected to atmospheric column chromatography on silica gel (with a mesh size ranging from 300 to 400), and eluted gradiently with petroleum ether/ethyl acetate system in ratios of 100:0, 95:5, 90:10, 80:20, 60:40 and 50:50 (v/v). The eluents were collected, subjected to vacuum distillation at 45° C., concentrated and washed with an organic solvent. The eluents from each elution section were combined and subjected to the above-mentioned atmospheric column chromatography on silica gel again, and eluted gradiently again with petroleum ether/ethyl acetate system in ratios of 100:0, 50:1, 20:1, 15:1, 10:1 and 5:1, (v/v). The eluents were collected and subjected to vacuum distillation at 45° C. The eluents from each elution section were combined again and further subjected to the gradient elution process with petroleum ether/ethyl acetate in ratios of 100:0, 50:1, 20:1, 15:1, 10:1 and 5:1 (v/v), to obtain Fumosorinone at the 5:1 elution section, namely, to obtain the protein tyrosine phosphatase inhibitor (a).

The yield of product was advantageously further increased by eluting the product in such manner.

Example 3: Preparation of the Product

This example differed from example 1 in the following procedures: the extractum sample, after being sufficiently adsorbed on the silica gel particles, was subjected to atmospheric column chromatography on silica gel (with a mesh size ranging from 300 to 400), and eluted gradiently with petroleum ether/ethyl acetate system in ratios of 100:0, 95:5, 90:10, 80:20, 60:40 and 50:50, (v/v). The eluents were collected, subjected to vacuum distillation at 45° C., concentrated and washed with an organic solvent. The fraction obtained from the above elution section with 80:20 of petroleum ether/ethyl acetate was further subjected to the above-mentioned atmospheric column chromatography on silica gel, and eluted gradiently with chloroform/methanol system in ratios of 100:0, 95:5 and 90:10 (v/v), to obtain Fumosorinone at the 90:10 elution section, namely, to obtain the protein tyrosine phosphatase inhibitor (a).

Example 4: Determination of the Structure of the Product

The structure of Fumosorinone was determined according to the spectral data of mass spectrum, NMR, spectrum and the like.

Data of UV spectrum: UV (MeOH) $\lambda_{max}$ nm: 367 (6.87), 265 (7.20), 209 (7.1.9).

Data of Infrared spectrum: $IRv^{KBr}_{max}$ cm$^{-1}$: 3267, 2960, 1643, 1516, 1446, 1268, 1218, 837, 758.

Data of Mass spectrum: Spectrum: HR-ESI-MS m/z: 500.24100 ([M+Na]$^+$, 500.24074 calcd. for $C_{29}H_{35}NNaO_5$).

For NMR data, see Table 2.

TABLE 2

Table 2. $^1$H-(600 MHz) and $^{13}$C-NMR (150 MHz) Data of Fumosorinone in CD$_3$OD$^1$

| | δ (H) | δ (C) | HMBC(H → C) |
|---|---|---|---|
| C(2) | | 158.6 | |
| C(3) | | 111.1 | |
| C(4) | | 166.5 | |
| C(5) | | 114.9 | |
| H—C(6) | 7.87 (s) | 137.9 | 1', 2, 4, 5 |
| C(7) | | 199.8 | |
| C(8) | | 137.1 | |
| H—C(9) | 6.94 (d, J = 9.8) | 141.8 | 7, 10, 24 |
| H—C(10) | 6.67(m) | 128.2 | 11 |
| H—C(11) | 6.67(m) | 142.9 | 10 |
| H—C(12) | 6.41 (dd, J = 15.2, 9.3) | 127.6 | 13 |
| H—C(13) | 6.45 (d, J = 15.3) | 143.4 | 12, 15 |
| C(14) | | 134.1 | |
| H—C(15) | 5.39 (d, J = 9.8) | 144.2 | 13, 16, 17 |
| H—C(16) | 2.68 (m) | 31.9 | 15 |
| CH$_2$(17) | 1.16 (m), 1.34 (m) | 46.1 | 18 |
| H—C(18) | 1.34 (m) | 33.7 | 17, 19, 21 |
| CH$_2$(19) | 1.16 (m), 1.34 (m) | 31.3 | 18, 20 |
| Me(20) | 0.88 (m) | 11.7 | 18, 19 |
| Me(21) | 0.88 (m) | 19.6 | 17, 18, 19 |
| Me(22) | 0.98 (d, J = 6.6) | 21.8 | 15, 16, 17 |
| Me(23) | 1.84 (s) | 12.7 | 13, 14, 15 |
| Me(24) | 2.06 (s) | 12.4 | 7, 8, 9 |
| C(1') | | 125.0 | |
| H—C(2') | 7.32 (d, J = 8.6) | 131.7 | 5, 2', 4' |
| H—C(3') | 6.84 (d, J = 8.6) | 116.4 | 1', 4' |
| C(4') | | 159.1 | |
| H—C(5') | 6.84 (d, J = 8.6) | 116.4 | 1', 4' |
| H—C(6') | 7.32 (d, J = 8.6) | 131.7 | 5, 4', 5' |

It can be determined from the above spectral data that Fumosorinone, i.e., the protein tyrosine phosphatase inhibitor (a) of the invention, has the following structure:

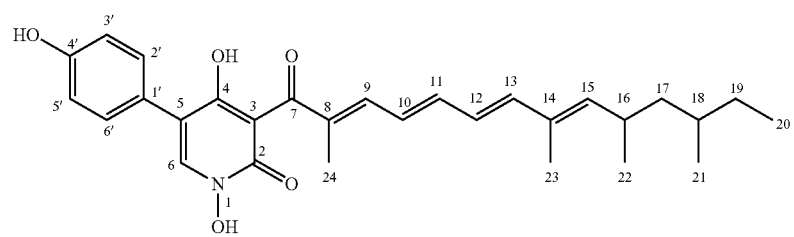 [SMILES: CCC(C)CC(C)/C=C(C)/C=C/C=C/C=C(\C)C(=O)c1c(O)c(-c2ccc(O)cc2)cn(O)c1=O]

Example 5: Use of the Product

According to the experiments described above, the use of the protein tyrosine phosphatase inhibitor (a) of the invention lies in the manufacture of a medicament, in particular a pharmaceutical composition for the treatment and prevention of diabetes, obesity and cancers. When it is used as a medicament, this compound can either be used directly or in the form of a pharmaceutical composition. The pharmaceutical composition may contain 0.1% to 99%, preferably 0.5% to 90% of the compound of the invention, and the balance of pharmaceutically acceptable carriers or excipients which are non-toxic and inert to human and animals. The pharmaceutically acceptable carriers or excipients may be one or more selected from the group consisting of fillers of solid, semi-solid and liquid diluents, or auxiliaries for drug products. The pharmaceutical composition is administered in the form of dosage per unit body weight. The medicament of the invention may be administered orally or by injection (intravenous or intramuscular injection). Oral administration may employ solid or liquid formulations thereof, such as powders, tablets, dragees, capsules, solutions, syrups and dropping pills. Injection administration may employ solid or liquid formulations thereof, such as powder injections and solution injections.

In the case of parenteral administration for human body, in order to achieve optimal effects, it is advantageous to employ an amount ranging from 0.1 to 10,000 µg/kg, preferably from 1 to 1,000 µg/kg, and in particular from 1 to 80 µg/kg body weight. In the case of oral administration, the amount is ranging from 0.2 to 10 mg/kg, preferably 0.6 to 6 mg/kg, and in particular from 1 to 5 mg/kg body weight. Nevertheless, depending on the body weight, administration route, individual response to the active compound, formulation type, and the time and intervals of administration, an amount deviated from said ranges may be necessary.

Example 6: Preparation of the Medicament

The compound Fumosorinone prepared according to example 1, was mixed with excipients at a weight ratio of 1:1 of the compound in crystal form to the excipients, and then granulated and compressed into tablets; or The compound Fumosorinone prepared according to example 1, was formulated into capsules by conventional methods for preparing capsules; or The compound Fumosorinone prepared according to example 1, was mixed with excipients at a weight ratio of 1:2 of the compound in crystal form to the excipients, and then granulated and compressed into tablets; or The compound Fumosorinone prepared according to example 1, was mixed with excipients at a weight ratio of 1:3 of the compound in crystal form to the excipients, and then granulated and compressed into tablets.

Example 7: Preparation of the Medicament

| Tablet: | |
|---|---|
| Fumosorinone | 100 mg |
| Starch | 100 mg |
| 17% of Corn syrup | appropriate amount |
| Magnesium stearate | appropriate amount |

Example 8: Preparation of the Medicament

| Capsule: | |
|---|---|
| Fumosorinone | 100 mg |
| Starch | 100 mg |
| Magnesium stearate | appropriate amount |

Preparation method: Fumosorinone was mixed with auxiliaries, and then sieved and thoroughly mixed in a proper container. The resulting mixture was placed into hard gelatin capsules.

Example 9: Preparation of the Medicament

| Ampoule: | |
|---|---|
| Fumosorinone | 50 mg |

Preparation method: Fumosorinone was dissolved in 2 ml of propylene glycol. After filtration, the resulting solution was placed into ampoules under sterile condition.

In addition, the protein tyrosine phosphatase inhibitor (a) of the invention may further be an isomer of the above-mentioned compound (a) or pharmaceutically acceptable derivative thereof. The pharmaceutically acceptable derivative is a commonly used pharmaceutical derivative which maintains the biological effectiveness of said compound (a). The selectable range and preparation method for such pharmaceutically acceptable derivative are common knowledge in the field of pharmacy. The illustrations as described above are only proposed as implementable technical solutions of the invention and would not serve as a single limitation to the technical solutions per se.

The invention claimed is:

1. A method for preparing a substantially isolated protein tyrosine phosphatase inhibitor having the following structural formula:

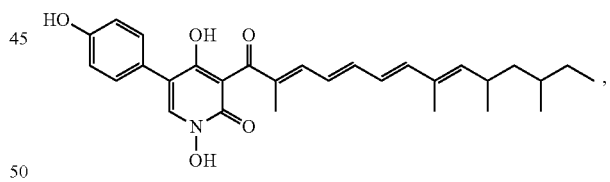

the method comprising: extracting a solid or liquid fermentation broth of entomogenous fungus *Isaria Fumosorosea Wize* with ethyl acetate, ethanol, methanol, or a mixed solvent of chloroform and methanol; separating the resulting extract by column chromatography on silica gel; and obtaining the substantially isolated protein tyrosine phosphatase inhibitor, Fumosorinone.

2. The method for preparing the protein tyrosine phosphatase inhibitor according to claim 1, further comprising:
   A. cultivating and preparing a fermentation broth by: inoculating the *Isaria Fumosorosea Wize* strain on a modified potato dextrose culture medium with an inoculation needle; culturing the mixture in a shaker at 150 rpm and at 26° C. for 7 days to obtain a seed broth; further inoculating the seed broth on a rice culture medium and culturing under light at 26° C. for 30 days to obtain a fermented product; wherein, the modified potato dextrose culture medium is formulated by the following steps: dissolving 200 parts by weight of peeled potato, 20 parts by weight of dextrose, 3 parts by weight of KH2PO₄, 1.5 parts by weight of MgSO₄, 0.1 parts by weight of citric acid, and 0.01 parts by weight of vitamin Bi in 1000 parts by weight of sterile water, and adjusting pH to 6.5 and sterilizing at 121° C. for 20 minutes; and the rice culture medium is formulated by the following steps: dissolving 80 parts by weight of rice in 100 parts by weight of sterile water, soaking for 12 hours, and then sterilizing at 121° C. for 30 minutes;

B. extracting and separating the fermented product by: extracting the fermented product by soaking it in an equal volume of ethyl acetate at room temperature for 48 hours; evaporating to dryness by vacuum distillation with a rotatory evaporator at 45° C. to obtain an extractum sample; mixing said extractum sample with 1.2 times by weight of silica gel having a mesh size of 100 to 200 under stirring; drying and grinding uniformly to obtain a powder, thereby absorbing said extractum sample onto particles of the silica gel; then performing atmospheric pressure column chromatography on silica gel having a mesh size ranging from 300 to 400, and eluting gradiently with petroleum ether/ethyl acetate system in ratios of 100:0, 95:5, 90:10, 80:20, 60:40 and 50:50 (v/v); collecting the eluents, evaporating by vacuum distillation at 45° C. concentrating and washing with an organic solvent; further subjecting the eluents with 80:20 of petroleum ether/ethyl acetate to the atmospheric pressure column chromatography on silica gel, and eluting gradiently with petroleum ether/ethyl acetate system in ratios of 100:0, 50:1, 20:1, 15:1, 10:1 and 5:1 (v/v) again; collecting the eluents, evaporating by vacuum distillation at 45° C. to obtain the protein tyrosine phosphatase inhibitor, Fumosorinone, at the 5:1 elution section.

3. The method for preparing the protein tyrosine phosphatase inhibitor according to claim 1, further comprising:

A. cultivating and preparing a fermentation broth of *Isaria Fumosorosea Wize* by: inoculating the *Isaria Fumosorosea Wize* strain on a modified potato dextrose culture medium with an inoculation needle; culturing the mixture in a shaker at 150 rpm and at 26° C. for 7 days to obtain a seed broth; further inoculating the seed broth on a rice culture medium and culturing under light at 26° C. for 30 days to obtain a fermented product; wherein, the modified potato dextrose culture medium is formulated by the following steps: dissolving 200 parts by weight of peeled potato, 20 parts by weight of dextrose, 3 parts by weight of KFI2PO₄, 1.5 parts by weight of MgSO₄, 0.1 parts by weight of citric acid, and 0.01 parts by weight of vitamin B-1 in 1000 parts by weight of sterile water, and adjusting pH to 6.5 and sterilizing at 121° C. for 20 minutes; and the rice culture medium is formulated by the following steps: dissolving 80 parts by weight of rice in 100 parts by weight of sterile water, soaking for 12 hours, and then sterilizing at 121° C. for 30 minutes;

B. extracting and separating the fermented product by: extracting the fermented product by soaking it in equal volume of ethyl acetate at room temperature for 48 hours; evaporating to dryness by vacuum distillation with a rotatory evaporator at 45° C. to obtain an extractum sample; mixing said extractum sample with 1.2 times by weight of silica gel having a mesh size of 100 to 200 under stirring; drying and grinding uniformly to obtain a powder, thereby absorbing said extractum sample onto particles of the silica gel particles; then performing atmospheric pressure column chromatography on silica gel having a mesh size ranging from 300 to 400, and eluting gradiently with petroleum ether/ethyl acetate system in ratios of 100:0, 95:5, 90:10, 80:20, 60:40 and 50:50 (v/v); collecting the eluents, evaporating by vacuum distillation at 45° C., concentrating and washing with an organic solvent; combining the eluents from each elution section, and performing the atmospheric pressure column chromatography on silica gel again, and eluting gradiently with petroleum ether/ethyl acetate system in ratios of 100:0, 50:1, 20:1, 15:1, 10:1 and 5:1 (v/v) again; collecting the eluents, evaporating by vacuum distillation at 45° C.; combining the eluents from each elution section again, and repeating the gradient elution with petroleum ether/ethyl acetate in ratios of 100:0, 50:1, 20:1, 15:1, 10:1 and 5:1 (v/v) to obtain the protein tyrosine phosphatase inhibitor, Fumosorinone, at the 5:1 elution section.

4. The method for preparing the protein tyrosine phosphatase inhibitor according to claim 1, further comprising:

A. cultivating and preparing a fermentation broth of *Isaria Fumosorosea Wize* by: inoculating the *Isaria Fumosorosea Wize* strain on a modified potato dextrose culture medium with an inoculation needle; culturing the mixture in a shaker at 150 rpm and at 26° C. for 7 days to obtain a seed broth; further inoculating the seed broth on a rice culture medium and culturing under light at 26° C. for 30 days to obtain a fermented product; wherein, the modified potato dextrose culture medium is formulated by the following steps: dissolving 200 parts by weight of peeled potato, 20 parts by weight of dextrose, 3 parts by weight of KH₂PO₄, 1.5 parts by weight of MgSO₄, 0.1 parts by weight of citric acid, and 0.01 parts by weight of vitamin Bi in 1000 parts by weight of sterile water, and adjusting pH to 6.5 and sterilizing at 121° C. for 20 minutes; and the rice culture medium is formulated by the following steps: dissolving 80 parts by weight of rice in 100 parts by weight of sterile water, soaking for 12 hours, and then sterilizing at 121° C. for 30 minutes;

B. extracting and separating the fermented product by: extracting the fermented product by soaking it in equal volume of ethyl acetate at room temperature for 48 hours; evaporating to dryness by vacuum distillation with a rotatory evaporator at 45° C. to obtain an extractum sample; mixing said extractum sample with 1.2 times by weight of silica gel having a mesh size of 100 to 200 under stirring; drying and grinding uniformly to obtain a powder, thereby absorbing said extractum sample onto particles of the silica gel particles; then performing atmospheric pressure column chromatography on silica gel having a mesh size ranging from 300 to 400, eluting gradiently with petroleum ether/ethyl acetate system in ratios of 100:0, 95:5, 90:10, 80:20, 60:40 and 50:50 (v/v); collecting the eluents, evaporating by vacuum distillation at 45° C., concentrating and washing with an organic solvent; further subjecting the eluents obtained from the above elution section with 80:20 of petroleum ether/ethyl acetate to the atmospheric pressure column chromatography on silica gel, and eluting gradiently with chloroform/methanol system in ratios of 100:0, 95:5 and 90:10 (v/v) to obtain the protein tyrosine phosphatase inhibitor, Fumosorinone, at the 90:10 elution section.

* * * * *